United States Patent
Watson et al.

(10) Patent No.: US 9,357,937 B2
(45) Date of Patent: Jun. 7, 2016

(54) SYSTEM AND METHOD FOR DETERMINING STROKE VOLUME OF AN INDIVIDUAL

(75) Inventors: James Nicholas Watson, Fife (GB); Paul Stanley Addison, Midlothian (GB)

(73) Assignee: Covidien LP, Mansfield, MA (US)

( * ) Notice: Subject to any disclaimer, the term of this patent is extended or adjusted under 35 U.S.C. 154(b) by 346 days.

(21) Appl. No.: 13/605,626

(22) Filed: Sep. 6, 2012

(65) Prior Publication Data

US 2014/0066785 A1 Mar. 6, 2014

(51) Int. Cl.
| | | |
|---|---|---|
| *A61B 5/0265* | (2006.01) |
| *A61B 5/0285* | (2006.01) |
| *A61B 5/029* | (2006.01) |
| *A61B 5/0295* | (2006.01) |

(52) U.S. Cl.
CPC ............ *A61B 5/0265* (2013.01); *A61B 5/029* (2013.01); *A61B 5/0285* (2013.01); *A61B 5/0295* (2013.01)

(58) Field of Classification Search
None
See application file for complete search history.

(56) References Cited

U.S. PATENT DOCUMENTS

| | | |
|---|---|---|
| 4,094,308 A | 6/1978 | Cormier |
| 4,282,655 A | 8/1981 | Tinman |
| 4,289,141 A | 9/1981 | Cormier |
| 4,450,527 A | 5/1984 | Sramek |
| 5,092,339 A | 3/1992 | Geddes |
| 5,178,151 A | 1/1993 | Sackner |
| 5,275,159 A | 1/1994 | Griebel |
| 5,331,960 A | 7/1994 | Krenzke |
| 5,408,327 A | 4/1995 | Geiler |
| 5,595,182 A | 1/1997 | Krivitski |
| 5,743,268 A | 4/1998 | Kabal |
| 5,817,010 A | 10/1998 | Hibl |
| 5,833,618 A | 11/1998 | Caro |
| 5,913,826 A | 6/1999 | Blank |
| 5,935,066 A | 8/1999 | Harris |
| 6,004,272 A | 12/1999 | Barry |
| 6,045,509 A | 4/2000 | Caro |
| 6,155,984 A | 12/2000 | Krivitski |

(Continued)

FOREIGN PATENT DOCUMENTS

| | | |
|---|---|---|
| EP | 0 537 383 | 4/1993 |
| EP | 0 841 034 | 5/1998 |

(Continued)

OTHER PUBLICATIONS

"Derivation of Respiratory Signals from Multi-lead ECGS, Moody," et al. (1985).

(Continued)

*Primary Examiner* — Long V Le
*Assistant Examiner* — Kevin Pontius
(74) *Attorney, Agent, or Firm* — Shvarts & Leiz LLP

(57) ABSTRACT

A system for determining stroke volume of an individual. The system includes a skew-determining module that is configured to calculate a first derivative of photoplethysmogram (PPG) signals of the individual. The first derivative forms a derivative waveform. The skew-determining module is configured to determine a skew metric of the first derivative, wherein the skew metric is indicative of a morphology of at least one pulse wave detected from blood flow of the individual in the derivative waveform. The system also includes an analysis module that is configured to determine a stroke volume of the individual. The stroke volume is a function of the skew metric of the first derivative.

16 Claims, 5 Drawing Sheets

(56) References Cited

U.S. PATENT DOCUMENTS

| | | |
|---|---|---|
| 6,292,686 B1 | 9/2001 | Chaiken |
| 6,371,921 B1 | 4/2002 | Caro |
| 6,389,306 B1 | 5/2002 | Chaiken |
| 6,503,206 B1 | 1/2003 | Li |
| 6,616,613 B1 | 9/2003 | Goodman |
| 6,719,705 B2 | 4/2004 | Mills |
| 6,740,072 B2 | 5/2004 | Starkweather |
| 6,754,523 B2 | 6/2004 | Toole |
| 6,758,822 B2 * | 7/2004 | Romano ............... 600/526 |
| 6,760,608 B2 | 7/2004 | Lynn |
| 6,776,764 B2 | 8/2004 | Pinsky |
| 6,816,266 B2 | 11/2004 | Varshneya |
| 6,869,402 B2 | 3/2005 | Arnold |
| 6,875,176 B2 | 4/2005 | Mourad |
| 7,022,077 B2 | 4/2006 | Mourad |
| 7,033,320 B2 | 4/2006 | Von Behren |
| 7,035,679 B2 * | 4/2006 | Addison et al. ............ 600/323 |
| 7,056,292 B2 | 6/2006 | Hutchinson |
| 7,171,271 B2 | 1/2007 | Koh |
| 7,220,230 B2 * | 5/2007 | Roteliuk et al. .......... 600/485 |
| 7,452,333 B2 | 11/2008 | Roteliuk |
| 7,462,152 B2 | 12/2008 | Kolluri |
| 7,615,011 B2 | 11/2009 | Sugo |
| 7,674,231 B2 | 3/2010 | McCombie |
| 7,704,209 B2 | 4/2010 | Bennett |
| 7,747,301 B2 | 6/2010 | Cheng |
| 7,785,263 B2 | 8/2010 | Roteliuk |
| 7,806,830 B2 | 10/2010 | Bernstein |
| 7,850,617 B2 | 12/2010 | Goedje |
| 7,881,762 B2 | 2/2011 | Kling |
| 7,894,869 B2 | 2/2011 | Hoaran |
| 7,899,510 B2 | 3/2011 | Hoaran |
| 7,976,472 B2 | 7/2011 | Kiani |
| 8,073,516 B2 | 12/2011 | Scharf |
| 8,073,518 B2 | 12/2011 | Chin |
| 8,187,197 B2 | 5/2012 | Shapira |
| 8,211,031 B2 | 7/2012 | Poupko |
| 8,825,428 B2 * | 9/2014 | Addison et al. ............ 702/98 |
| 2002/0022785 A1 | 2/2002 | Romano |
| 2002/0082485 A1 | 6/2002 | Faithfull |
| 2003/0167012 A1 | 9/2003 | Friedman |
| 2005/0080345 A1 | 4/2005 | Finburgh |
| 2005/0085707 A1 | 4/2005 | Korsten |
| 2005/0124903 A1 | 6/2005 | Roteliuk |
| 2005/0240087 A1 | 10/2005 | Keenan |
| 2006/0184051 A1 | 8/2006 | Hempstead |
| 2006/0224053 A1 | 10/2006 | Black |
| 2007/0093702 A1 | 4/2007 | Yu |
| 2007/0213625 A1 | 9/2007 | Nayak |
| 2007/0249949 A1 | 10/2007 | Hadley |
| 2008/0082004 A1 | 4/2008 | Banet |
| 2008/0119329 A1 | 5/2008 | Punkka |
| 2008/0139958 A1 | 6/2008 | Uemura |
| 2008/0183232 A1 | 7/2008 | Voss |
| 2008/0287815 A1 | 11/2008 | Chon |
| 2009/0099459 A1 | 4/2009 | Svanberg |
| 2009/0149762 A1 | 6/2009 | Ou Yang et al. |
| 2009/0177110 A1 | 7/2009 | Lyden |
| 2009/0198140 A1 | 8/2009 | Riobo Aboy et al. |
| 2009/0204012 A1 | 8/2009 | Joeken |
| 2009/0240119 A1 | 9/2009 | Schwaibold |
| 2009/0326353 A1 | 12/2009 | Watson |
| 2009/0326388 A1 | 12/2009 | Watson |
| 2009/0326395 A1 | 12/2009 | Watson |
| 2010/0016739 A1 | 1/2010 | Shelley |
| 2010/0049007 A1 | 2/2010 | Sterling |
| 2010/0049071 A1 | 2/2010 | Goor |
| 2010/0069765 A1 * | 3/2010 | Keren ............... 600/504 |
| 2010/0081895 A1 | 4/2010 | Zand |
| 2010/0152547 A1 | 6/2010 | Sterling |
| 2010/0152591 A1 | 6/2010 | Yu |
| 2010/0160794 A1 | 6/2010 | Banet |
| 2010/0191128 A1 | 7/2010 | Shelley |
| 2010/0210924 A1 | 8/2010 | Parthasarathy |
| 2010/0249542 A1 | 9/2010 | Thijs |
| 2010/0249559 A1 | 9/2010 | Lovejoy |
| 2010/0249612 A1 | 9/2010 | Cohen |
| 2010/0268090 A1 | 10/2010 | Rubinstein |
| 2010/0268101 A1 | 10/2010 | Sugo |
| 2010/0268518 A1 | 10/2010 | Sugo |
| 2010/0298689 A1 | 11/2010 | Wang |
| 2010/0324388 A1 | 12/2010 | Moon |
| 2010/0324431 A1 | 12/2010 | Addison |
| 2010/0324827 A1 | 12/2010 | Addison |
| 2011/0009754 A1 | 1/2011 | Wenzel |
| 2011/0009755 A1 | 1/2011 | Wenzel |
| 2011/0026784 A1 | 2/2011 | Van Slyke |
| 2011/0034813 A1 | 2/2011 | Cohen |
| 2011/0040345 A1 | 2/2011 | Wenzel |
| 2011/0060234 A1 | 3/2011 | Zhou |
| 2011/0060531 A1 | 3/2011 | Sugo |
| 2011/0077532 A1 | 3/2011 | Kim |
| 2011/0087115 A1 | 4/2011 | Sackner |
| 2011/0098112 A1 | 4/2011 | LeBoeuf |
| 2011/0098546 A1 | 4/2011 | Farazi |
| 2011/0105918 A1 | 5/2011 | Fortin |
| 2011/0172504 A1 | 7/2011 | Wegerich |
| 2011/0209915 A1 | 9/2011 | Telfort |
| 2011/0224564 A1 | 9/2011 | Moon |
| 2011/0270097 A1 | 11/2011 | Aboy |
| 2011/0301436 A1 | 12/2011 | Teixeira |
| 2012/0022350 A1 | 1/2012 | Teixeira |
| 2012/0029320 A1 | 2/2012 | Watson |
| 2012/0029361 A1 | 2/2012 | Addison |
| 2012/0029363 A1 | 2/2012 | Lund |
| 2012/0046557 A1 | 2/2012 | Kiani |
| 2012/0053433 A1 | 3/2012 | Chamoun |
| 2012/0053469 A1 | 3/2012 | Melker |
| 2012/0065485 A1 | 3/2012 | Benni |
| 2012/0065527 A1 | 3/2012 | Gill |
| 2012/0065528 A1 | 3/2012 | Gill |
| 2012/0078069 A1 | 3/2012 | Melker |
| 2012/0109018 A1 | 5/2012 | Gertner |
| 2012/0136261 A1 | 5/2012 | Sethi |
| 2012/0136605 A1 | 5/2012 | Addison |
| 2012/0172723 A1 | 7/2012 | Gertner |
| 2012/0172732 A1 | 7/2012 | Meyer, Jr. |
| 2014/0057940 A1 * | 2/2014 | Mankowski et al. ......... 600/485 |

FOREIGN PATENT DOCUMENTS

| | | |
|---|---|---|
| EP | 1 443 856 | 2/2006 |
| EP | 1 769 737 | 4/2007 |
| EP | 1 884 189 | 2/2008 |
| EP | 2 281 508 | 2/2011 |
| EP | 2 047 794 | 2/2012 |
| EP | 2 217 140 | 2/2012 |
| WO | WO 91/13589 | 9/1991 |
| WO | WO 94/14372 | 7/1994 |
| WO | WO 97/47236 | 12/1997 |
| WO | WO 98/41279 | 9/1998 |
| WO | WO 02/03076 | 1/2002 |
| WO | WO 03/082099 | 10/2003 |
| WO | WO 2004/071292 | 8/2004 |
| WO | WO 2005/055825 | 6/2005 |
| WO | WO 2006/100676 | 9/2006 |
| WO | WO 2007/109065 | 9/2007 |
| WO | WO 2008/094598 | 8/2008 |
| WO | WO 2008/144404 | 11/2008 |
| WO | WO 2008/144525 | 11/2008 |
| WO | WO 2009/009761 | 1/2009 |
| WO | WO 2009/014420 | 1/2009 |
| WO | WO 2009/101140 | 8/2009 |
| WO | WO 2010/001231 | 1/2010 |
| WO | WO 2010/045556 | 4/2010 |
| WO | WO 2010/096475 | 8/2010 |
| WO | WO 2010/111073 | 9/2010 |
| WO | WO/2010/124034 | 10/2010 |
| WO | WO 2010/146326 | 12/2010 |
| WO | WO 2010/146327 | 12/2010 |
| WO | WO 2011/047211 | 4/2011 |
| WO | WO 2011/050066 | 4/2011 |
| WO | WO 2011/051822 | 5/2011 |
| WO | WO 2011/060220 | 5/2011 |

(56) References Cited

FOREIGN PATENT DOCUMENTS

| WO | WO 2011/077294 | 6/2011 |
| --- | --- | --- |
| WO | WO 2011/080190 | 7/2011 |
| WO | WO 2011/080194 | 7/2011 |
| WO | WO2011/087927 | 7/2011 |
| WO | WO 2011/089488 | 7/2011 |
| WO | WO 2012/009350 | 1/2012 |
| WO | WO 2012/014065 | 2/2012 |
| WO | WO 2012/015426 | 2/2012 |
| WO | WO 2012/027613 | 3/2012 |
| WO | WO 2012/032413 | 3/2012 |
| WO | WO 2012/032536 | 3/2012 |
| WO | WO 2012/052926 | 4/2012 |
| WO | WO 2012/075322 | 6/2012 |
| WO | WO 2012/076957 | 6/2012 |

OTHER PUBLICATIONS

"Photoplethsmography and its application in clinical physiological measurement," Physiol. Meas. 28 (2007).

"Venus Oximetry," Signa Vitae 2007.

"Near-Infrared Spectrometry (NIRS) and Venous-side Monitoring of the Circulation," Hoffman.

"On the Analysis of Fingertip Photoplethysmogram Signals," Elgendi, Current Cardiology Reviews, 2012.

"A Computer Based Photoplethysmographic Vascular Analyzer Through Derivatives," Gonzalez, et al, Computers in Cardiology (2008).

"Noninvasive Assessment of the Digital Volume Pulse: Comparison with the Peripheral Pressure Pulse," Millasseau, et al., Journal of the American Heart Association (2000).

"Non-Invasive Estimation of Cardiac Output from Finger Photoplethysmogram Based on Windkessel Model," Poon, Bulletin of Advance Technology Research, vol. 4, No. 6 (2010).

"Non-constrained Blood Pressure Monitoring Using ECG and PPG for Personal Healthcare," Yoon, et al, (2008).

"How to measure heart rate?" Vogel, et al. Eur. J. Clin Paramacol (2004) 60.461-466.

"Resting Heart Rate in Cardiovascular Disease," Fox, et al. Journal of the Amercan College of Cardiology vol. 50, No. 9 (2007).

"Why measure resting heart rate?" Nauman (2012).

"The shape and dimensions of photoplethsymographic pulse waves; a measurement repeatability study," Marcinkevics, et al. Acta Universitatis Latviensis,vol. 753, Bilology, pp. 99-106 (2009).

"Monitoring of Reactive Hyperemia Using Photoplethysmographic Pulse Amplitude and Transit Time," Selvavaj, et al. Journal of Clinical Monitoring and Computing 23:315-322 (2009).

"Photoacoustic thermal diffusion flowmetry," Sheinfeld, et al., Biomedical Optics Express vol. 3, No. 4 (2012).

"Flow dependent photothermal modulation of the photoacoustic response," Sheinfeld, et al, Photonos Plus Ultrasound: Imaging and Sensing (2012).

"Relation between repiratory variations in pulse oximetry plethysmographic waveform amplitude and arterial pulse pressure in ventilated patients," Cannesson, et al. Ciritical Care (2005).

"Pulse oximeter plethysmograph variation and its relationship to the arterial waveform in mechanically ventilated childer," Chandler, et al. J. Clin. Monit. Comput. (2012).

"Variations in Arterial Blood Pressure and Photoplethysmography During Mechanical Ventilation," Natalani, et al., Technology, Computing, and Simulation, vol. 103, No. 5, (2006).

International Search Report and Written Opinion of the International Searching Authority for counterpart PCT application PCT/US2013/057457.

* cited by examiner

SYSTEM AND METHOD FOR DETERMINING STROKE VOLUME OF AN INDIVIDUAL Embodiments of the present disclosure generally relate to physiological signal processing and, more particularly, to processing photoplethysmogram (PPG) signals to determine a stroke volume of an individual.

BACKGROUND

Stroke volume is typically defined as the volume of blood that is ejected from one of the ventricles (e.g., the left ventricle) during contraction of the heart. The stroke volume of an individual may decrease during certain situations (e.g., blood loss during surgery) or as certain cardiovascular conditions develop. In some cases, stroke volume itself may be used to identify an emergency situation or a health condition. For example, when the stroke volume of a patient is very low, such as during excessive blood loss, the patient's body may be unable to circulate a sufficient amount of blood to the patient's organs and organ failure may occur. Accordingly, medical personnel typically desire an accurate method for determining stroke volume so that corrective action may be taken when the stroke volume falls below a designated value.

Various methods for determining stroke volume may be used, such as oesophageal Doppler monitoring, transpulmonary thermodilution, lithium indicator dilution, pulse power analysis, and pulse contour analysis. Pulse contour analysis may provide a less invasive method of determining stroke volume. In pulse contour analysis, the stroke volume is estimated by analyzing the pulse waves that are detected from a peripheral artery or from another anatomical location, such as a finger tip. Various models have been developed that estimate the stroke volume by analyzing the pulse waves. For example, one proposed model determines elements that estimate characteristic impedance, Windkessel compliance, and peripheral resistance of the patient. However, under certain circumstances (e.g., very high or low blood pressure, particular heart abnormalities, or during certain medical procedures), one or more of the above methods used to estimate stroke volume may have limitations that render the estimate unreliable.

SUMMARY

Certain embodiments provide a system for determining a stroke volume of an individual. The system includes a skew-determining module that is configured to calculate a first derivative of photoplethysmogram (PPG) signals of the individual. The first derivative forms a derivative waveform. The skew-determining module is configured to determine a skew metric of the first derivative, wherein the skew metric is indicative of a morphology of at least one pulse wave detected from blood flow of the individual in the derivative waveform. The system also includes an analysis module that is configured to determine a stroke volume of the individual. The stroke volume is a function of the skew metric of the first derivative.

The skew metric may be a calculated value that is indicative of a distribution of values in a data set that includes the data points that define the pulse wave in the derivative waveform. The skew metric may be determined for each pulse wave or for a pulse-ensemble average that is based on a number of the pulse waves. In some embodiments, the pulse wave may be approximately defined from a first upstroke to a second, adjacent upstroke, wherein each of the first and second upstrokes corresponds to an increase in blood volume caused by a heart beat.

In certain embodiments, the skew metric may be determined using at least one of Pearson's skewness, Fisher-Pearson standardized moment coefficient, quartile-based measurements, distance skewness, Cyhelsky's skewness coefficients, or a morphological metric of the derivative waveform.

The system may also include a PPG sensor that is operably coupled to the monitor. The pulse waves may be pulse waves detected from a finger of the individual.

In some embodiments, the stroke volume may be based on at least one of a constant or a coefficient. The constant and/or the coefficient may be determined by observed historical data and/or characteristics of the PPG signals.

In some embodiments, the skew metric may be determined a plurality of times within a designated period of time to determine a change in the skew metric. For example, the analysis module may calculate a difference between a first calculated skew metric and a later determined second skew metric. The change in the skew metric may be used to determine a change in the stroke volume.

Certain embodiments provide a method for determining a stroke volume of an individual. The method may include acquiring PPG signals of the individual. The PPG signals may correspond to pulse waves detected from blood flow of the individual. The method may also include calculating a first derivative of the PPG signals. The first derivative may form a derivative waveform. The method may also include determining a skew metric of the first derivative, wherein the skew metric is indicative of a morphology of at least one of the pulse waves in the derivative waveform. The method may also include determining a stroke volume of the individual, wherein the stroke volume is a function of the skew metric of the first derivative.

Certain embodiments provide a tangible and non-transitory computer readable medium that includes one or more sets of instructions configured to direct a monitor to acquire PPG signals of the individual. The PPG signals may correspond to pulse waves detected from blood flow of the individual. The monitor may be directed to calculate a first derivative of the PPG signals. The first derivative may form a derivative waveform. The monitor may also be directed to determine a skew metric of the first derivative, wherein the skew metric is indicative of a morphology of at least one of the pulse waves in the derivative waveform. The monitor may also be directed to determine a stroke volume of the individual. The stroke volume may be a function of the skew metric of the first derivative.

Certain embodiments provide a system for determining a stroke volume of an individual. The system may include a monitor configured to obtain photoplethysmogram (PPG) signals of the individual. The PPG signals may correspond to pulse waves detected from blood flow of the individual. The monitor may include a skew-determining module that is configured to calculate a first derivative of the PPG signals. The first derivative forms a derivative waveform. The skew-determining module may also be configured to determine a skew metric of the first derivative, wherein the skew metric is indicative of a morphology of at least one of the pulse waves in the derivative waveform. The monitor may also include an analysis module that is configured to determine a stroke volume of the individual. The stroke volume may be a function of the skew metric of the first derivative.

One or more embodiments of the present disclosure may allow for a quick, simple, and more reliable determination of stroke volume for an individual. One or more embodiments may also facilitate non-invasive and/or continuous monitoring of stroke volume by using a pulse oximeter. In certain embodiments, the skew metric may be determined from the derivative of a pulse-ensemble average of the PPG signals, which may improve an overall measurement quality. A change in skew metric over a period of time may also be determined to calculate a change in stroke volume. Moreover, a change of the skew metric over time may be used to confirm a direction of pressure change trending over time. Alternatively or in addition to the above, the skew metric may be used to calculate cardiac output and other cardiac parameters.

In one or more embodiments, the skew-determining methods described herein may be used in conjunction with other methods/models for determining stroke volume or cardiac output.

Certain embodiments may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

DETAILED DESCRIPTION

Figure 1:
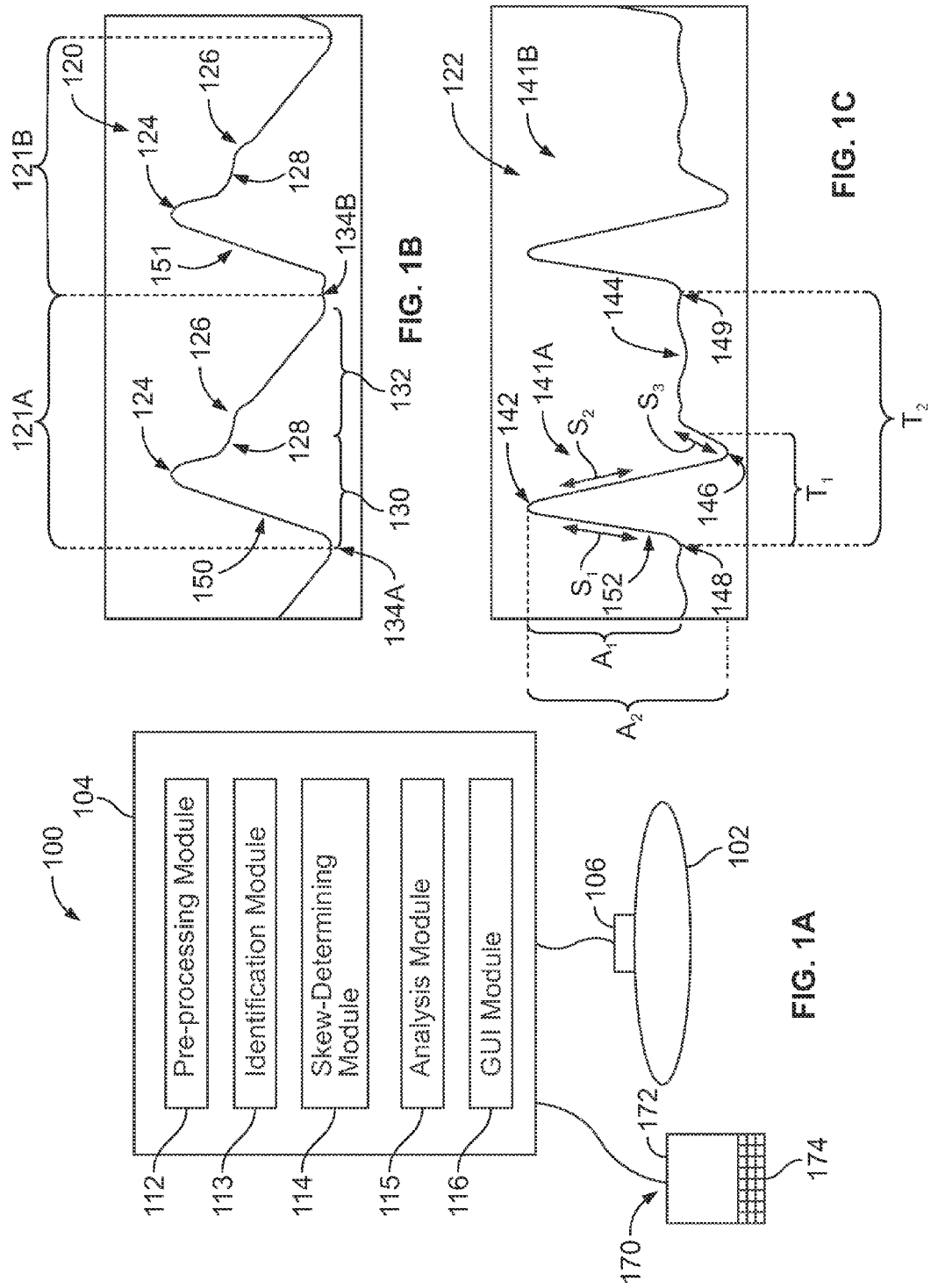
FIG. 1A illustrates a simplified block diagram of a system configured to determine a cardiovascular parameter of an individual, according to an embodiment.
FIG. 1B illustrates a photoplethysmogram (PPG) waveform, according to an embodiment.
FIG. 1C illustrates a first derivative of the PPG waveform, according to an embodiment.

FIG. 1A illustrates a simplified block diagram of a system 100 configured to determine a cardiovascular parameter of an individual. The system 100 is configured to acquire physiological signals (e.g., photoplethysmogram (PPG) signals or signals that describe blood pressure) from an individual 102 (e.g., a patient) and analyze the physiological signals to determine a cardiovascular parameter, such as stroke volume or cardiac output. The physiological signals may include features that describe cardiac activity in which the heart undergoes a number of cardiac cycles. In certain embodiments, the physiological signals include PPG signals obtained by a pulse oximeter. As shown in FIG. 1A, the system 100 may include a monitor 104 (or computing system) and a sensor 106 that is operably coupled to the monitor 104 and configured to detect the PPG signals. The PPG signals may correspond to pulse waves detected from blood flow in a circulatory system of the individual. The pulse waves may be caused by contractions of the heart.

The system 100 may be a PPG system that can measure changes in blood volume through at least one anatomical portion or location (e.g., finger, toe, ear, thumb web, wrist, and/or ankle). A typical example of a PPG system is a pulse oximetry system, such as the pulse oximetry system 310 shown in FIG. 4. Other PPG systems, however, exist and may be used with embodiments described herein. The sensor 106 may include a probe having one or more light sources and one or more light detectors that are coupled to the individual 102. The light source(s) provide an incident light that is scattered, absorbed, reflected, and/or transmitted by the blood. The light detector(s) detect an amount of light that may correspond to blood volume. For example, as the volume of blood increases at the anatomical location, the light is attenuated more and, as such, a smaller amount of light is detected. FIG. 1B illustrates, according to an embodiment, a representative PPG waveform 120 based on the PPG signals acquired by the sensor 106. The PPG waveform 120 describes or represents volumetric changes in the blood vessel(s) at the anatomical location. The repetitive changes in the PPG waveform correspond to pulse waves that are generated by contractions of the heart.

As shown in FIG. 1A, the monitor 104 may include one or more components for analyzing and/or processing the physiological signals. For example, the monitor 104 may include a pre-processing module 112, an identification module 113, a skew-determining module 114, an analysis module 115, and a graphical user interface (GUI) module 116. As used herein, a "module" may include hardware components (e.g., processor, controller), software components, or a combination thereof including any associated circuitry.

The pre-processing module 112 is configured to receive raw PPG signals that are obtained from the individual 102 and remove unwanted signal data (e.g., noise) from the raw PPG signals. For example, raw PPG signals may include artifacts caused by motion of the individual relative to the light detector, instrumentation bias (e.g., bias by amplifiers used in the PPG system), powerline interference, low amplitude PPG signals, or other unwanted signal data. The pre-processing module 112 may also include one or more filters, such as a bandpass filter (0.5 Hz-7.5 Hz), that filter the PPG signals. The pre-processing module 112 is configured to remove the noise to provide clearer and/or cleaner PPG signals for processing or analysis by the other components. For example, the pre-processing module 112 may provide signals that are easier to analyze and identify pulse waves therefrom. The PPG waveform 120 shown in FIG. 1B is based on PPG signals that have been pre-processed.

The skew-determining module 114 is configured to calculate a first derivative of the PPG signals (or the PPG waveform 120) and determine a skew metric of the first derivative. Calculating a first derivative of the PPG signals may also be described as differentiating the PPG signals or the PPG waveform 120. The first derivative, which may be referred to as PPG' or dPPG/dt, indicates how much the PPG signals are changing with respect to time (e.g., rate of change). Differentiation of the PPG signals may provide a first derivative waveform 122 (hereinafter referred to as "the derivative waveform") as shown in FIG. 1C. The repetitive changes in the derivative waveform also correspond to the pulse waves that are generated by contractions of the heart.

The identification module 113 may be configured to identify the pulse waves by analyzing the PPG signals, which may include analyzing at least one of the PPG waveform 120 or the derivative waveform 122. In some embodiments, the identification module 113 is part of the pre-processing module 112 or part of the skew-determining module 114. The identification module 113 may analyze the PPG signals to identify the valid pulse waves before or after the PPG signals have been at least partially pre-processed. The identification module 113 may also analyze the PPG signals to identify the valid pulse waves before or after the PPG signals have been differentiated.

For instance, the identification module 113 may analyze the PPG waveform 120 and identify the pulse waves in the PPG waveform 120. To this end, the identification module 113 may examine the PPG waveform 120 to identify one or more waveform features in the PPG signals. For instance, a series of data points corresponding to PPG values may provide a waveform over time, such as the PPG waveform 120. A waveform feature may be an identifiable point, segment, or characteristic of the PPG waveform 120 (e.g., peak, trough (or foot), notch, amplitude, slope of a designated segment, threshold, etc.) that may be relied upon in analysis of the PPG signals. In many cases, a waveform feature of the PPG waveform 120 corresponds to a known physiological activity (e.g., excitation of heart muscles, closure or opening of valves, maximum volume of blood at an anatomical location, etc.). The identification module 113 may examine the data points, or a select number of data points (e.g., a segment of the waveform), to confirm that the data points are caused by a designated event of a cardiac cycle and are not a result of noise or other unwanted event, such as when the sensor 106 is being adjusted.

The data points associated with valid pulse waves may then be used by the other components of the system 100. In some embodiments, the data points that are not identified as corresponding to pulse waves may not be considered in subsequent analysis.

In other embodiments, the identification module 113 may analyze the first derivative waveform 122 to identify the pulse waves from the derivative waveform. The pulse waves in the derivative waveform 122 may be identified using similar methods as described above with respect to the pulse waves in the PPG waveform 120. For example, the identification module 113 may analyze the derivative waveform 122 and identify a waveform feature, which may be an identifiable point, segment, or characteristic of the derivative waveform 122 (e.g., peak, trough (or foot), amplitude, slope of a designated segment, threshold, etc.) that may be relied upon for identifying a pulse wave.

Also shown in FIG. 1A, the system 100 may include a user interface 170 that has a display 172. The user interface 170 may include hardware, firmware, software, or a combination thereof that enables a user to directly or indirectly control operation of the system 100 and the various components thereof. The display 172 is configured to display one or more images, such as one or more of the PPG and first derivative waveforms 120, 122. The display 172 may also be configured to show the current stroke volume (not shown) and/or the current cardiac output (not shown). In some embodiments, the user interface 170 may also include one or more input devices 174, such as a physical keyboard, mouse, touchpad, and/or touch-sensitive display. The user interface 170 may be operatively connected to the GUI module 116 and receive instructions from the GUI module 116 to display designated images on the display 172. The user interface 170 may also include a printer or other device for providing (e.g. printing) a report.

In FIG. 1B, the PPG waveform 120 illustrates two adjacent pulse waves 121A, 121B that correspond to two adjacent heart beats of the individual 102. As shown with respect to the pulse wave 121A, a pulse wave may include a pulsatile component 130 and a baseline component 132. The pulsatile component 130 represents a pressure wave generated from the heart to a point of detection, such as a finger where a PPG sensor may be located. The pulsatile component 130 may be synchronized (e.g., occur at the same frequency) with the contractions of the heart, although the pulsatile component 130 is detected after the corresponding pressure wave has propagated to the point of detection. The baseline component 132 represents one or more reflected pressure waves that are reflected back to the point of detection. The baseline component 132 may correlate to a relative vascularization of the tissue.

Each identified pulse wave 121 of the PPG waveform 120 may include a primary or systolic peak 124, a trailing or diastolic maximum 126, and a dicrotic segment 128 that extends therebetween. In some cases, the dicrotic segment 128 forms a notch (referred to as the dicrotic notch) that is located between the systolic peak 124 and the diastolic maximum 126. The diastolic maximum 126 may be referred to as the diastolic peak 126 when the dicrotic notch 128 exists. The systolic peak 124 is caused by the pulsatile component 130, and the diastolic maximum or peak 126 may be caused by a combination of the pulsatile component 130 and the baseline component 132. In some cases, the diastolic maximum or peak 126 is significantly or exclusively caused by the baseline component 132.

Also shown in FIG. 1B, the PPG waveform 120 includes a first foot 134A that corresponds to the beginning of the pulsatile component 130 of the pulse wave 121A, which may also be characterized as the beginning of the pulse wave 121A. The beginning of the pulse wave 121A is a first upstroke 150 in the PPG waveform 120 that may correspond to an increase in blood volume caused by a heartbeat (or contraction of the heart). The PPG waveform 120 also includes a second foot 134B that corresponds to the beginning of the pulsatile component of the pulse wave 121B. The beginning of the pulse wave 121B is a second upstroke 151 in the PPG waveform 120. In some embodiments, a time period of an individual pulse wave 121 may be defined between the first and second feet 134A, 134B. The identification module 113 may identify the feet 134A, 134B by identifying the first upstroke 150 and the second, adjacent upstroke 151. However, in other embodiments, the time periods and/or the individual pulse waves may be defined between other points, features, or events in the PPG waveform 120. For example, pulse waves may be counted by identifying the systolic peaks 124.

In FIG. 1C, the derivative waveform 122 illustrates two adjacent pulse waves 141A, 141B. The pulse waves 141A, 141B of the derivative waveform 122 correlate to the pulse waves 121A, 121B of the PPG waveform 120 in time. More specifically, the pulse waves 141A, 141B represent the differentiated portions of the PPG signals or the PPG waveform 120 that correspond to the pulse waves 121A, 121B.

Skewness is a measure of the symmetry or asymmetry of a distribution of values in a data set. In this case, the data set includes the data points that define a pulse wave in the derivative waveform. Each data point has a respective value. For instance, the pulse wave 141A in the derivative waveform 122 may be defined as extending from a foot 148 to a foot 149 in FIG. 1C. Each data point that defines the pulse wave 141A in the derivative waveform 122 has a value. The data points proximate to a derivative peak 142 have a positive value, and the data points proximate to a derivative trough 146 have a negative value. The skewness for the pulse wave 141A is a measure of the symmetry of the distribution of the values. With respect to the pulse wave 141A, the skew metric is positive. The skewness of the pulse wave 141A is indicative of a morphology of the pulse wave 141A.

Under at least some circumstances, a skewness of the first derivative of the pulse waves 121A, 121B may correlate with stroke volume of the individual 102. Accordingly, a skew metric may be indicative of a morphology of the pulse wave 141 (or the pulse wave 121) that, in turn, may provide information regarding the stroke volume. In certain embodiments, the skew metric is determined (e.g., calculated) using one or more skewness formulas or models. For example, the skew metric may be determined using at least one of Pearson's skewness, a Fisher-Pearson standardized moment coefficient, a mean-to-median ratio, quartile-based measurements, a distance skewness, Cyhelsky's skewness coefficients.

With the skew metric determined, an analysis module 115 may determine the stroke volume of the individual 102. More specifically, the stroke volume may be a function of the skew metric.

Alternatively or in addition to the above skew metric calculations, the skew metric may be determined by determining a morphological metric of the derivative waveform 122. As used herein, "a morphological metric," includes a calculated value of a waveform feature of the derivative waveform 122 or a calculated relationship between one or more waveform features of the derivative waveform 122.

FIG. 1C illustrates various waveform features (or structures) that may relate to or be indicative of the skewness of the derivative waveform 122. With respect to the pulse wave 141A and by way of example only, the pulse wave 141A includes an upstroke 154 that, similar to the upstrokes 150, 151 (FIG. 1B), indicates a beginning of the pulse wave 141A in the derivative waveform 122. The pulse wave 141A also includes first and second amplitudes $A_1$, $A_2$. The first amplitude $A_1$ may represent a difference between a derivative peak 142 and a baseline portion 144 of the derivative waveform 122. The second amplitude $A_2$ may represent a difference between a derivative trough 146 and the derivative peak 142. Other waveform features may include a first time period $T_1$ that may approximately correspond to a width of the pulsatile component 130 in the derivative waveform 122, and a second time period $T_2$ that may approximately correspond to a duration of the pulse wave 141A. It should be noted that various modifications or adjustments may be made to the above waveform features. For example, the time period $T_1$ may be defined between a derivative foot 148 of the pulse wave 141A and the derivative trough 146. In some embodiments, an increase in the time period $T_1$ relative to the time period $T_2$ may indicate that the skewness is also increasing.

Other examples of waveform features may include different slopes of the derivative waveform 122. As shown in FIG. 1C, the pulse wave 141A may include a primary slope $S_1$ that has a positive value, a secondary slope $S_2$ that has a negative value, and a tertiary slope $S_3$ that has a positive value. The above examples are not intended to be limiting and other waveform features of the derivative waveform 122 may be used. For example, a length of a waveform segment that extends between the derivative peak and the derivative trough may be used.

Figure 2:
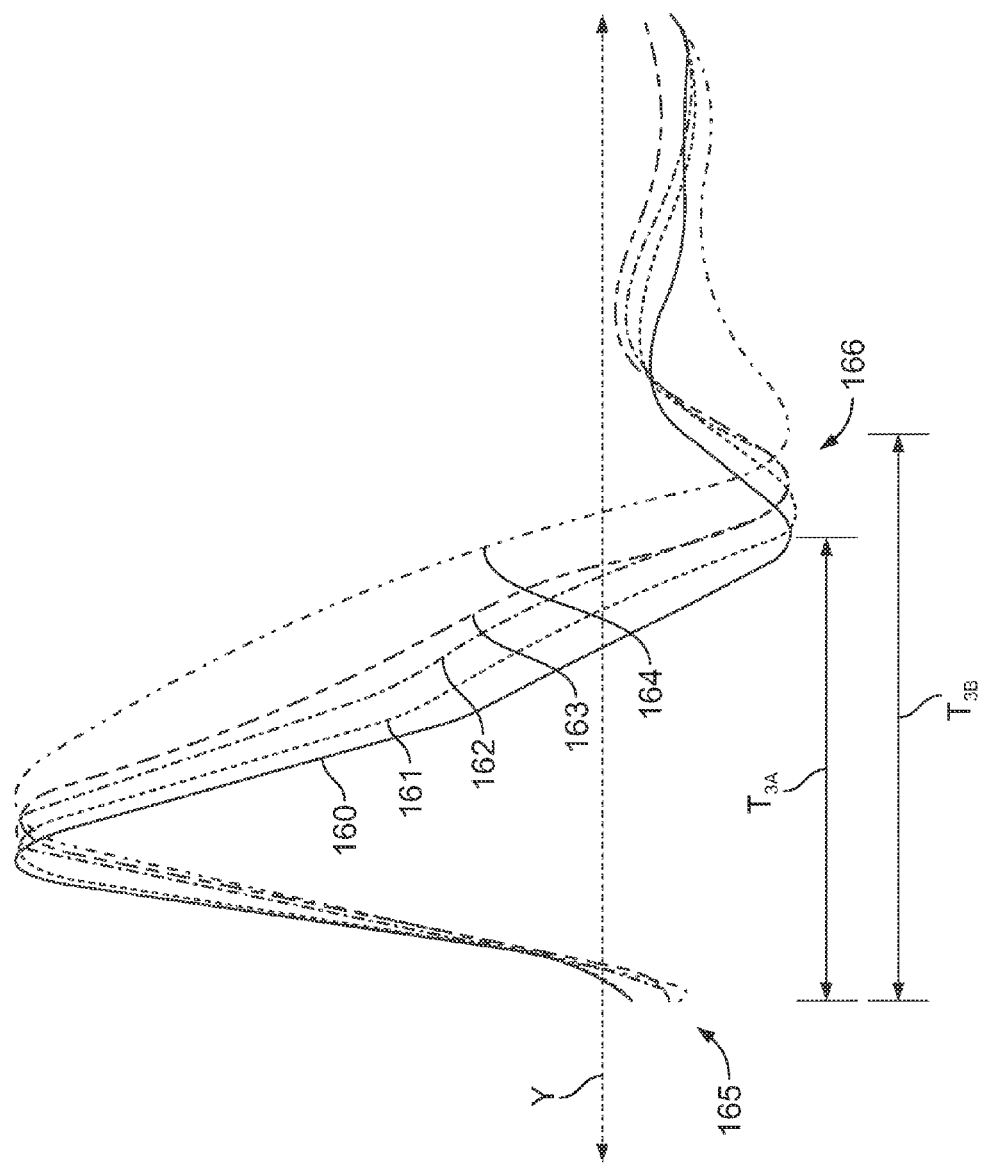
FIG. 2 illustrates a plurality of pulse waves from a first derivative of the PPG waveform that have different morphologies, according to an embodiment.

To illustrate the changing morphology of a pulse wave, FIG. 2 shows a number of pulse waves 160-164 from a differentiated PPG waveform (or the derivative waveform). Each of the pulse waves 160-164 has a derivative foot 165 and a derivative trough 166. A time period $T_3$ may be measured between the derivative foot and trough 165, 166 of the corresponding pulse wave. Each of the pulse waves 160-164 is associated with a greater pressure than the preceding pulse wave. The pulse wave 160 corresponds to the least pressure of the pulse waves 160-164, and the pulse wave 164 corresponds to the greatest pressure of the pulse waves 160-164. As shown, the pulse wave 160 has the time period $T_{3A}$, and the pulse wave 164 has the time period $T_{3B}$. FIG. 2 illustrates that, as the pressure increases, the time period $T_3$ between the corresponding foot and trough of the pulse wave increases.

A y-axis is shown in FIG. 2. The derivative values above the y-axis are positive and the derivative values below the y-axis are negative. Notably, as the time period $T_3$ increases for a pulse wave, the number of derivative values that are positive increases in proportion to the number of negative values. Consequently, as the time period $T_3$ increases for a pulse wave, the skew metric will become more positive. As such, the skew metric changes with a change in pressure. A change in pressure may correlate with a change in stroke volume when the heart rate is constant and the systemic vascular resistance is constant. Accordingly, the skew metric may trend with the stroke volume and be used in a function to determine the stroke volume. Alternatively, a change in skew metric may be used to determine a change in stroke volume.

The skew-determining module 114 (FIG. 1) may use one or more of the waveform features and/or one or more of the skewness models described above to determine a skew metric. The skew metric, in turn, may be used by the analysis module 115 to determine the stroke volume of the individual 102 and the cardiac output. In some embodiments, the formula or model used to determine at least one of the skew metric, the stroke volume, or the cardiac output may include constants and/or coefficients that are computed from relationships derived from observed historical data (e.g. relationships with patient demographic data, such as BMI, height, weight, and the like) and/or measured signal characteristics (e.g. heart rate, a skew metric of the PPG waveform 120, another skew metric of the derivative waveform 122). In some embodiments, the constants and/or coefficients may be derived in whole or in part by calibration through, for example, dilution methods for obtaining cardiac output from which stroke volume can be derived if heart rate is known. The cardiac output may be determined using the stroke volume. Cardiac output may be defined as the product of stroke volume and heart rate.

Figure 3:
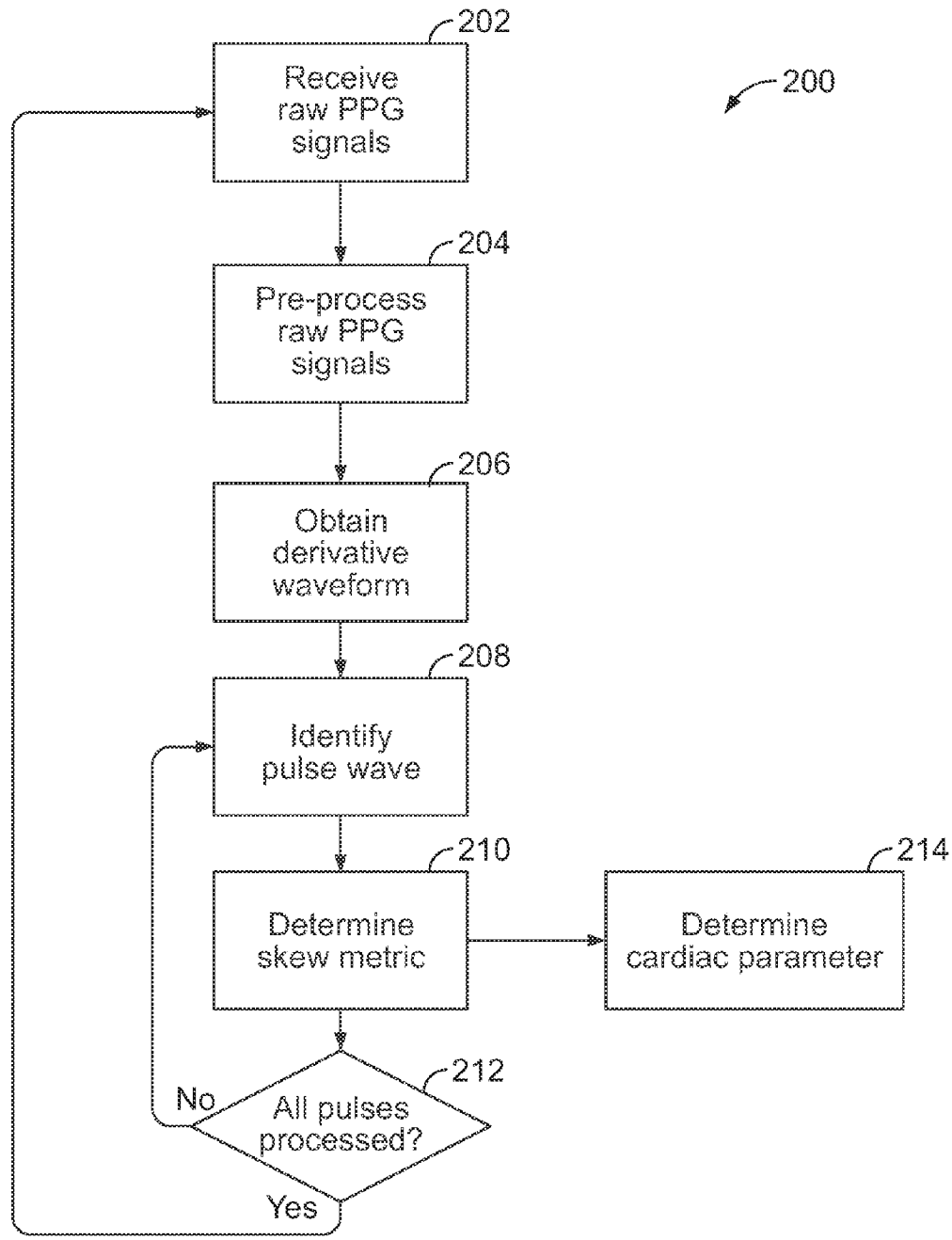
FIG. 3 illustrates a flow chart of a method of determining a stroke volume of an individual, according to an embodiment.

FIG. 3 illustrates a flow chart of a method 200 of determining a stroke volume of an individual. The method 200 may be performed by the system 100 (FIG. 1) or the system 310 (shown in FIG. 4). The method 200 includes receiving at 202 raw PPG signals from a sensor, such as the sensor 106 (FIG. 1). The sensor 106 may be coupled to an anatomical location where reliable PPG signals may be obtained. Exemplary anatomical locations include one or more fingers of an individual or foot/ankle of an infant, but other anatomical locations may be used. The raw PPG signals may be pre-processed at 204. During the pre-processing, the raw PPG signals may be filtered using, for example, a bandpass filter (e.g., 0.5 Hz-7.5 Hz). The pre-processing at 204 may include removing unwanted signal data (e.g., noise) from the raw PPG signals. The pre-processing at 204 may provide a validated or processed PPG waveform that includes one or more pulse waves similar to the pulse waves 121 described with respect to FIG. 1B.

At 206, the PPG waveform may be differentiated to obtain a derivative waveform. At 208, one or more pulse waves may be identified in the derivative waveform. The pulse waves may be identified by locating designated reference or waveform features. For example, with reference to FIG. 1C, the individual pulse wave 141A of the derivative waveform 122 may extend from the foot 148 of the pulse wave 141A to the foot 149 of the adjacent pulse wave 141B. Identification of a pulse wave, however, may be accomplished in other manners. For example, other repetitive waveform features (e.g., derivative peaks) may be identified.

In other embodiments, the identification at 208 of the pulse waves may occur before the PPG waveform is differentiated at 206. In such cases, the pulse waves of the PPG waveform may be identified and then the PPG waveform (or the individual pulse waves) may be differentiated.

Having identified the pulse waves, a skew metric may be determined at 210. The skew metric may be determined using at least one of Pearson's skewness, Fisher-Pearson standardized moment coefficient, quartile-based measurements, distance skewness, Cyhelsky's skewness coefficients, or a morphological metric of the derivative waveform. By way of example, the following equation may be used to calculate the skew metric:

$$= \frac{n \sum_{i}^{n} (PPG_i' - \mu_{pulse})^3}{(n-1)(n-2)\sigma_{pulse}^3} \quad \text{Equation (1)}$$

where n is a sample size (e.g., a number of points describing the pulse wave); PPG' is a vector of length n holding the points that describe the derivative of the pulse wave for which skew is being calculated; $\mu_{pulse}$ is a mean PPG value of the pulse wave; and $\sigma_{pulse}$ the standard deviation of the PPG values over the pulse wave.

Additional equations to determine skew metric may also include:

$$\frac{\text{mean}}{\text{median}} \quad \text{Equation (2)}$$

$$\frac{\text{max} - \text{median}}{\text{median} - \text{min}} \quad \text{Equation (3)}$$

$$\frac{Q3 - \text{median}}{\text{median} - Q1} \quad \text{Equation (4)}$$

$$\frac{\text{max} - Q3}{Q1 - \text{min}} \quad \text{Equation (5)}$$

$$\frac{\frac{1}{2}(\text{min} + \text{max})}{\text{median}} \quad \text{Equation (6)}$$

$$\frac{\frac{1}{2}(Q1 + Q3)}{\text{median}} \quad \text{Equation (7)}$$

$$\frac{\frac{1}{2}(\text{min} + \text{max})}{\frac{1}{2}(Q1 + Q3)} \quad \text{Equation (8)}$$

$$\frac{\text{min} + Q1 + \text{median} + Q3 + \text{max}}{5} \quad \text{Equation (9)}$$

$$\frac{\frac{1}{n} \sum (x - \bar{x})^3}{\sqrt{\frac{1}{n} \sum (x - \bar{x})^2}^3} \quad \text{Equation (10)}$$

$$\frac{3(\text{mean} - \text{median})}{\text{standard deviation}} \quad \text{Equation (11)}$$

$$\frac{(Q3 - \text{median}) - (\text{median} - Q1)}{Q3 - Q1} \quad \text{Equation (12)}$$

where mean is the average of the values in the data set (e.g., values of the data points that define the pulse wave in the corresponding waveform); median is the median value in the data set; max is the maximum value in the data set; min is the minimum value in the data set; standard deviation is the standard deviation of the data set; Q1 is the first quartile; Q3 is the third quartile; x is a corresponding value of a data point; and $\bar{x}$ is the sample mean.

In addition, the formula or model used to determine the skew metric may include constants and/or coefficients that are computed from relationships derived from observed historical data (e.g. relationships with patient demographic data, such as BMI, height, weight, and the like) and/or measured signal characteristics (e.g. heart rate, a skew metric of the PPG waveform 120, another skew metric of the derivative waveform 122). In some embodiments, the constants and/or coefficients may be derived in whole or in part by calibration through, for example, dilution methods for obtaining cardiac output from which stroke volume can be derived if heart rate is known.

The skew metric determined at 210 may be based on a single individual pulse wave or the skew metric may be determined using a plurality of pulse waves of the derivative waveform. For example, the method 200 may include querying at 212 whether each of the pulse waves in a segment or portion of the derivative waveform has been processed. If yes, the method 200 may return to 202, in which the raw PPG are received. If no, the method 200 may identify the next pulse wave(s) and determine a skew metric therefrom.

The determined skew metric may also be an average skew metric that is based on an average of the skew metrics for two or more pulse waves of the derivative waveform. In some embodiments, the skew metric may be determined from the derivative of a pulse-ensemble average of the PPG signals. In such embodiments, after the pulse wave(s) is/are identified at 208, the pulse-ensemble average may be updated and the skew metric of the pulse-ensemble average may be determined again.

At 214, a cardiac parameter may be determined. The cardiac parameter may be stroke volume and/or cardiac output, which may also include a change in stroke volume or a change in cardiac output. By way of example, the cardiac parameters of stroke volume (SV) and cardiac output (CO) may be determined using the following equations:

$$CO = SV \times HR \quad \text{Equation (13)}$$

$$SV = f(\text{skew metric}) \quad \text{Equation (14)}$$

$$SV = \alpha \times \text{Skew Metric} + \beta \quad \text{Equation (15)}$$

$$CO = (\alpha \times \text{Skew Metric} + \beta) \times HR \quad \text{Equation (16)}$$

where f( . . . ) indicates a functional relationship with the terms within the parentheses, HR is heart rate, and $\alpha$ and $\beta$ are empirically-determined constants that may be determined through clinical examinations of individuals and dependent upon the nature of the subject (e.g., the patient) and/or the nature of the signal detecting devices. The constants $\alpha$ and $\beta$ may be computed from relationships derived from observed historical data (e.g. relationships with patient demographic data, such as body-mass index (BMI), height, weight, and the like) and/or measured signal characteristics (e.g. heart rate, a skew metric of the PPG waveform 120, another skew metric of the derivative waveform 122). In some embodiments, the constants and/or coefficients may be derived in whole or in part by calibration through, for example, dilution methods for obtaining cardiac output from which stroke volume can be derived if heart rate is known.

In some embodiments, the skew metric may be determined a plurality of times within a designated period of time to determine a change in the skew metric. For example, the analysis module may calculate a difference between a first calculated skew metric and a later determined second skew metric. In some cases, the skew metric may be continuously determined (e.g., at least six times in a minute) to calculate the change in the skew metric. The change in the skew metric may be used to determine a change in the stroke volume and may also be used to determine a change in cardiac output.

Figure 4:
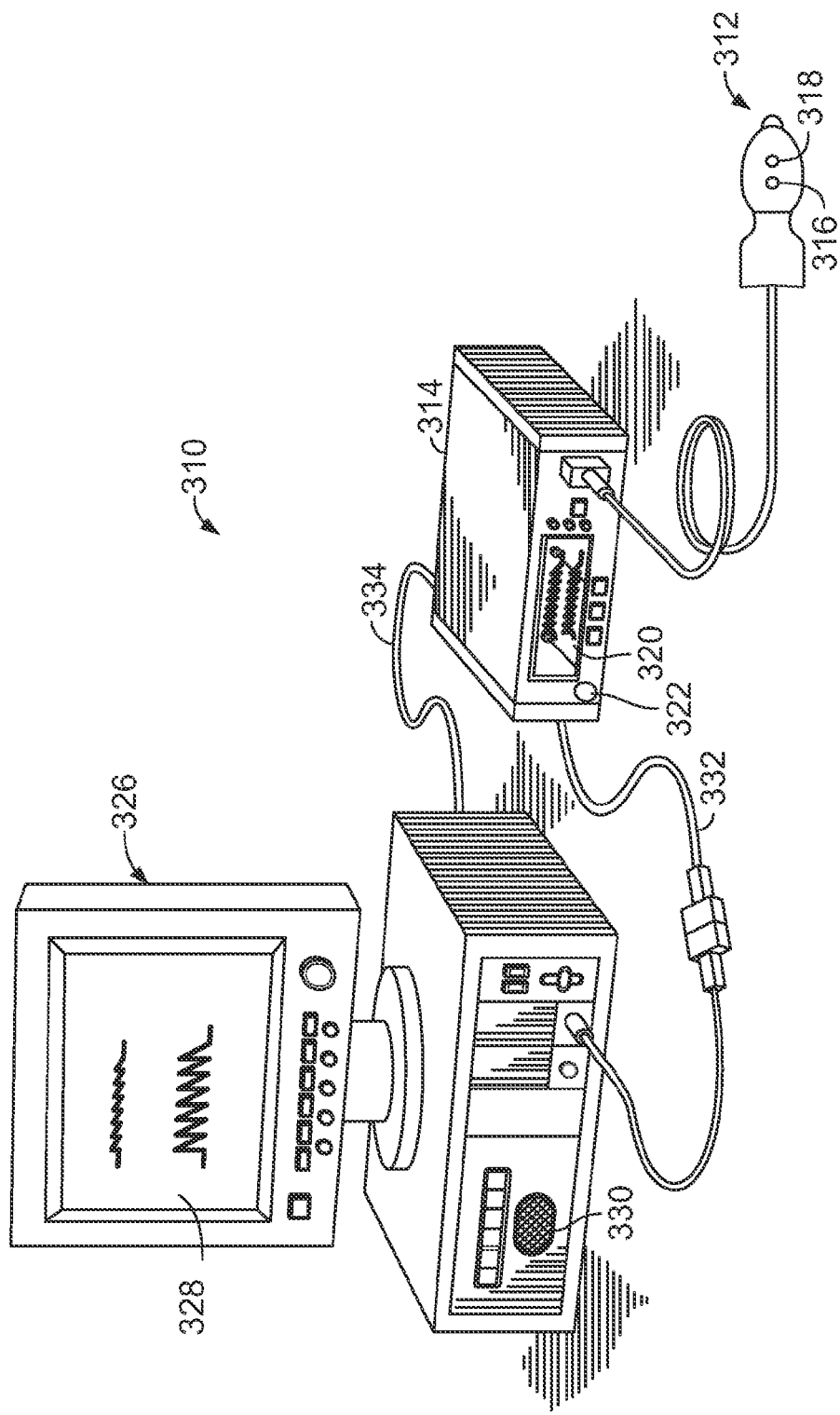
FIG. 4 illustrates an isometric view of a PPG system, according to an embodiment.

FIG. 4 illustrates an isometric view of a PPG system 310, according to an embodiment. The PPG system 310 may be configured to, among other things, determine stroke volume of an individual. The PPG system 310 may be configured to analyze and/or process PPG signals as described above with respect to FIGS. 1A-1C and the system 100.

The PPG system 310 may be a pulse oximetry system, for example. The system 310 may include a PPG sensor 312 and a PPG monitor 314. The PPG sensor 312 may include an emitter 316 configured to emit light into tissue of an individual. For example, the emitter 316 may be configured to emit light at two or more wavelengths into the tissue of the individual. The PPG sensor 312 may also include a detector 318 that is configured to detect the emitted light from the emitter 316 that emanates from the tissue after passing through the tissue. In other embodiments, the system 310 may include a plurality of sensors forming a sensor array in place of the PPG sensor 312. In such embodiments, the sensor array may include a complementary metal oxide semiconductor (CMOS) sensor, a charged coupled device (CCD) sensor, or a combination thereof.

The emitter 316 and the detector 318 may be configured to be located at opposite sides of a digit, such as a finger or toe, in which case the light that is emanating from the tissue passes completely through the digit. The emitter 316 and the detector 318 may be arranged so that light from the emitter 316 penetrates the tissue and is reflected by the tissue into the detector 318, such as a sensor designed to obtain pulse oximetry data (e.g., PPG signals).

The sensor 312 (or sensor array) may be operatively connected to and draw power from the monitor 314. Optionally, the sensor 312 may be wirelessly connected to the monitor 314 and include a battery or similar power supply (not shown). The monitor 314 may be similar to the monitor 104 described above and may be configured to analyze physiological signals and calculate physiological parameters based at least in part on data received from the sensor 312 relating to light emission and detection. Alternatively, the calculations may be performed by and within the sensor 312 and the result of the oximetry reading may be passed to the monitor 314. Additionally, the monitor 314 may include a display 320 configured to display the physiological parameters (e.g., current HR, stroke volume, cardiac output, and other physiological parameters) or information about the system 310. The monitor 314 may also include a speaker 322 configured to provide an audible sound that may be used in various other embodiments, such as for example, sounding an audible alarm in the event that physiological parameters are outside a predefined normal range.

The system 310 may also include a multi-parameter workstation 326 operatively connected to the monitor 314. The workstation 326 may be or include a computing system 330, such as standard computer hardware. The computing system 330 may be similar to the monitor (or computing system) 104 described above and include one or more modules and control units, such as processing devices that may include one or more microprocessors, microcontrollers, integrated circuits, memory, such as read-only and/or random access memory, and the like. The workstation 326 may include a display 328, such as a cathode ray tube display, a flat panel display, such as a liquid crystal display (LCD), light-emitting diode (LED) display, a plasma display, a touch-sensitive display, or any other type of display. The computing system 330 of the workstation 326 may be configured to calculate physiological parameters and to show information from the monitor 314 and from other medical monitoring devices or systems (not shown) on the display 328. For example, the workstation 326 may be configured to display an estimate of an individual's blood oxygen saturation generated by the monitor 314 (referred to as an $SpO_2$ measurement), HR information from the monitor 314, and blood pressure from a blood pressure monitor (not shown) on the display 328.

The monitor 314 may be communicatively coupled to the workstation 326 via a cable 334 and/or 332 that is coupled to a sensor input port or a digital communications port, respectively and/or may communicate wirelessly with the workstation 326. Additionally, the monitor 314 and/or workstation 326 may be coupled to a network to enable the sharing of information with servers or other workstations. The monitor 314 may be powered by a battery or by a conventional power source such as a wall outlet.

Figure 5:
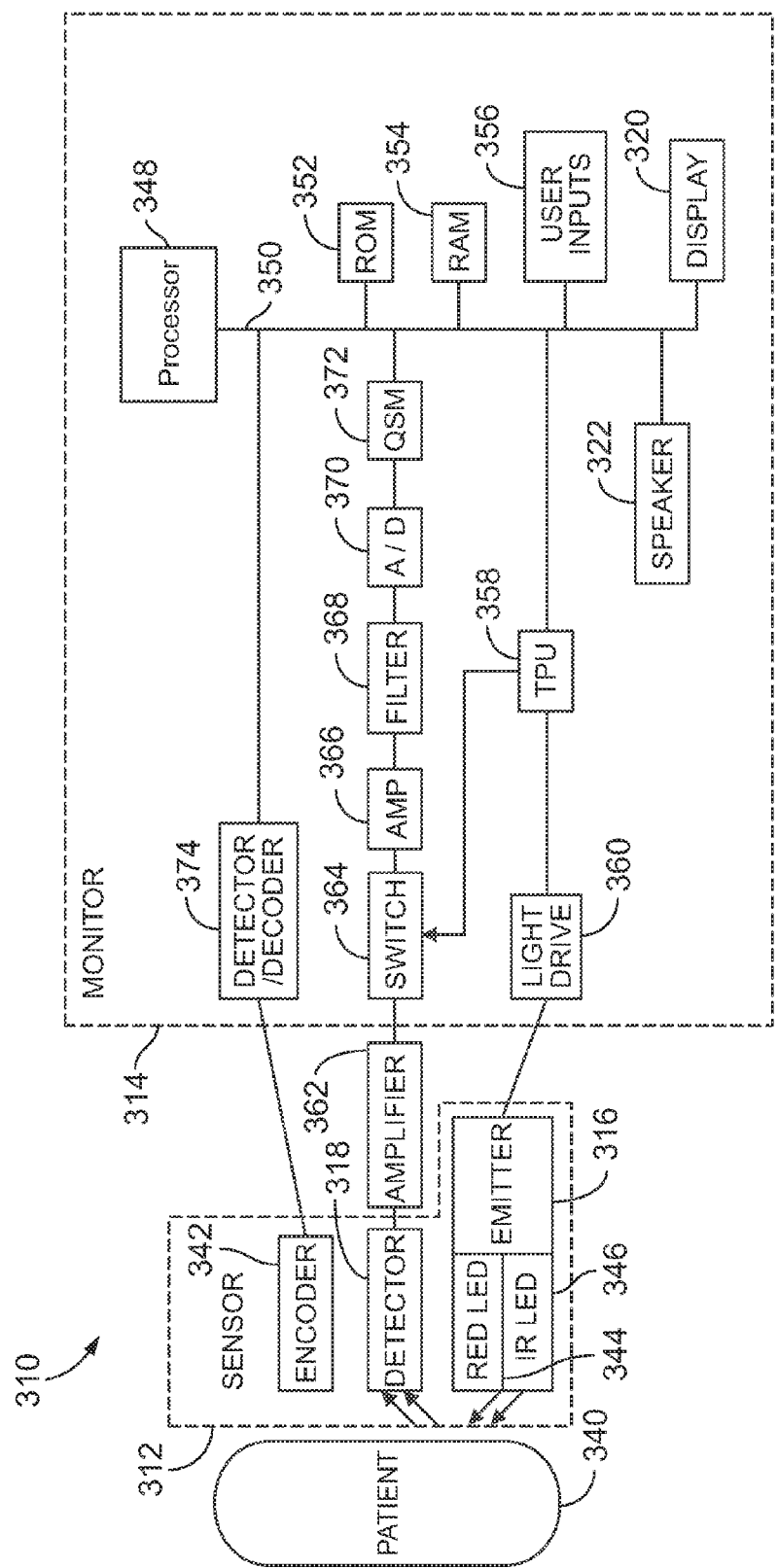
FIG. 5 illustrates a simplified block diagram of a PPG system, according to an embodiment.

FIG. 5 illustrates a simplified block diagram of the PPG system 310, according to an embodiment. When the PPG system 310 is a pulse oximetry system, the emitter 316 may be configured to emit at least two wavelengths of light (for example, red and infrared) into tissue 340 of an individual. Accordingly, the emitter 316 may include a red light-emitting light source such as a red light-emitting diode (LED) 344 and an infrared light-emitting light source such as an infrared LED 346 for emitting light into the tissue 340 at the wavelengths used to calculate the individual's physiological parameters. For example, the red wavelength may be between about 600 nm and about 700 nm, and the infrared wavelength may be between about 800 nm and about 1000 nm. In embodiments where a sensor array is used in place of single sensor, each sensor may be configured to emit a single wavelength. For example, a first sensor may emit a red light while a second sensor may emit an infrared light.

As discussed above, the PPG system 310 is described in terms of a pulse oximetry system. However, the PPG system 310 may be various other types of systems. For example, the PPG system 310 may be configured to emit more or less than two wavelengths of light into the tissue 340 of the individual. Further, the PPG system 310 may be configured to emit wavelengths of light other than red and infrared into the tissue 340. As used herein, the term "light" may refer to energy produced by radiative sources and may include one or more of ultrasound, radio, microwave, millimeter wave, infrared, visible, ultraviolet, gamma ray or X-ray electromagnetic radiation. The light may also include any wavelength within the radio, microwave, infrared, visible, ultraviolet, or X-ray spectra, and that any suitable wavelength of electromagnetic radiation may be used with the system 310. The detector 318 may be configured to be specifically sensitive to the chosen targeted energy spectrum of the emitter 316.

The detector 318 may be configured to detect the intensity of light at the red and infrared wavelengths. Alternatively, each sensor in the array may be configured to detect an intensity of a single wavelength. In operation, light may enter the detector 318 after passing through the tissue 340. The detector 318 may convert the intensity of the received light into an electrical signal. The light intensity may be directly related to the absorbance and/or reflectance of light in the tissue 340. For example, when more light at a certain wavelength is absorbed or reflected, less light of that wavelength is received from the tissue by the detector 318. After converting the received light to an electrical signal, the detector 318 may send the signal to the monitor 314, which calculates physiological parameters based on the absorption of the red and infrared wavelengths in the tissue 340.

In an embodiment, an encoder 342 may store information about the sensor 312, such as sensor type (for example, whether the sensor is intended for placement on a forehead or digit) and the wavelengths of light emitted by the emitter 316. The stored information may be used by the monitor 314 to select appropriate algorithms, lookup tables and/or calibration coefficients stored in the monitor 314 for calculating physiological parameters of an individual. The encoder 342 may store or otherwise contain information specific to an individual, such as, for example, the individual's age, weight, and diagnosis. The information may allow the monitor 314 to determine, for example, individual-specific threshold ranges related to the individual's physiological parameter measurements, and to enable or disable additional physiological parameter algorithms. The encoder 342 may, for instance, be a coded resistor that stores values corresponding to the type of sensor 312 or the types of each sensor in the sensor array, the wavelengths of light emitted by emitter 316 on each sensor of the sensor array, and/or the individual's characteristics. Optionally, the encoder 342 may include a memory in which one or more of the following may be stored for communication to the monitor 314: the type of the sensor 312, the wavelengths of light emitted by emitter 316, the particular wavelength each sensor in the sensor array is monitoring, a signal threshold for each sensor in the sensor array, any other suitable information, or any combination thereof.

Signals from the detector 318 and the encoder 342 may be transmitted to the monitor 314. The monitor 314 may include a general-purpose control unit, such as a microprocessor 348 connected to an internal bus 350. The microprocessor 348 may be configured to execute software, which may include an operating system and one or more applications, as part of performing the functions described herein. A read-only memory (ROM) 352, a random access memory (RAM) 354, user inputs 356, the display 320, and the speaker 322 may also be operatively connected to the bus 350. The control unit and/or the microprocessor 348 (or other parts of the monitor 314) may include a pre-processing module, a identification module, a rate-determining module, an analysis module, and a GUI module, such as those described above.

The RAM 354 and the ROM 352 are illustrated by way of example, and not limitation. Any suitable computer-readable media may be used in the system for data storage. Computer-readable media are configured to store information that may be interpreted by the microprocessor 348. The information may be data or may take the form of computer-executable instructions, such as software applications, that cause the microprocessor to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

The monitor 314 may also include a time processing unit (TPU) 358 configured to provide timing control signals to a light drive circuitry 360, which may control when the emitter 316 is illuminated and multiplexed timing for the red LED 344 and the infrared LED 346. The TPU 358 may also control the gating-in of signals from the detector 318 through an amplifier 362 and a switching circuit 364. The signals are sampled at the proper time, depending upon which light source is illuminated. The received signal from the detector 318 may be passed through an amplifier 366, a low pass filter 368, and an analog-to-digital converter 370. The digital data may then be stored in a queued serial module (QSM) 372 (or buffer) for later downloading to RAM 354 as QSM 372 fills up. In an embodiment, there may be multiple separate parallel paths having amplifier 366, filter 368, and A/D converter 370 for multiple light wavelengths or spectra received. In some embodiments, the amplifier 366, the low pass filter 368, and the analog-to-digital converter 370 are part of a pre-processing module.

The microprocessor 348 may be configured to determine the individual's physiological parameters, such as $SpO_2$ and pulse rate, using various algorithms and/or look-up tables based on the value(s) of the received signals and/or data corresponding to the light received by the detector 318. The signals corresponding to information about an individual, and regarding the intensity of light emanating from the tissue 340 over time, may be transmitted from the encoder 342 to a decoder 374. The transmitted signals may include, for example, encoded information relating to individual characteristics. The decoder 374 may translate the signals to enable the microprocessor 348 to determine the thresholds based on algorithms or look-up tables stored in the ROM 352. The user inputs 356 may be used to enter information about the individual, such as age, weight, height, diagnosis, medications, treatments, and so forth. The display 320 may show a list of values that may generally apply to the individual, such as, for example, age ranges or medication families, which the user may select using the user inputs 356.

As noted, the PPG system 310 may be a pulse oximetry system. A pulse oximeter is a medical device that may determine oxygen saturation of blood. The pulse oximeter may indirectly measure the oxygen saturation of an individual's blood (as opposed to measuring oxygen saturation directly by analyzing a blood sample taken from the individual) and changes in blood volume in the skin. Ancillary to the blood oxygen saturation measurement, pulse oximeters may also be used to measure the pulse rate (or HR) of an individual as described above. Pulse oximeters typically measure and display various blood flow characteristics including, but not limited to, the oxygen saturation of hemoglobin in arterial blood.

A pulse oximeter may include a light sensor, similar to the sensor 312, that is placed at a site on an individual, typically a fingertip, toe, forehead or earlobe, or in the case of a neonate, across a foot. The pulse oximeter may pass light using a light source through blood perfused tissue and photoelectrically sense the absorption of light in the tissue. For example, the pulse oximeter may measure the intensity of light that is received at the light sensor as a function of time. A signal representing light intensity versus time or a mathematical manipulation of this signal (for example, a scaled version thereof, a log taken thereof, a scaled version of a log taken thereof, and/or the like) may be referred to as the photoplethysmograph (PPG) signal. In addition, the term "PPG signal," as used herein, may also refer to an absorption signal (for example, representing the amount of light absorbed by the tissue) or any suitable mathematical manipulation thereof. The light intensity or the amount of light absorbed may then be used to calculate the amount of the blood constituent (for example, oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with lower oxygen saturation. By comparing the intensities of two wavelengths at different points in the pulse cycle, it is possible to estimate the blood oxygen saturation of hemoglobin in arterial blood.

The PPG system 310 and pulse oximetry are further described in United States Patent Application Publication No. 2012/0053433, entitled "System and Method to Determine $SpO_2$ Variability and Additional Physiological Parameters to Detect Individual Status," United States Patent Application Publication No. 2010/0324827, entitled "Fluid Responsiveness Measure," and United States Patent Application Publication No. 2009/0326353, entitled "Processing and Detecting Baseline Changes in Signals," all of which are hereby incorporated by reference in their entireties.

Various embodiments described herein provide a tangible and non-transitory (for example, not an electric signal) machine-readable medium or media having instructions recorded thereon for a processor or computer to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer," "computing system," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "computing system".

The computer, computing system, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

As discussed above, embodiments of the present disclosure may allow for a quick, simple, and/or more reliable determination of stroke volume for an individual. Embodiments may also facilitate a non-invasive and/or continuous monitoring of stroke volume through, for example, the use of a pulse oximeter. In certain embodiments, the skew metric may be determined from the derivative of a pulse-ensemble average of the PPG signals. Alternatively, the skew metric may be determined from a single individual pulse wave. Moreover, a change of the skew metric over time may be used to confirm a direction of pressure change trending over time. Alternatively or in addition to the above, the skew metric may be used to calculate cardiac output and other cardiac parameters.

It is to be understood that the above description is intended to be illustrative, and not restrictive. For example, the above-described embodiments (and/or aspects thereof) may be used in combination with each other. In addition, many modifications may be made to adapt a particular situation or material to the teachings without departing from its scope. While the dimensions, types of materials, and the like described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A pulse oximetry system for determining stroke volume of an individual, the system comprising:
   a pulse oximetry sensor configured to generate a photoplethysmogram (PPG) signal, wherein the pulse oximetry sensor detects light attenuated by the individual; and a pulse oximeter coupled to the pulse oximetry sensor, the pulse oximeter comprising:
a skew-determining circuitry configured to calculate a first derivative of the PPG signal of the individual, the first derivative forming a derivative waveform, wherein the skew-determining circuitry is configured to determine a skew metric of the first derivative, wherein the skew metric is indicative of a symmetry or asymmetry of at least one pulse wave detected from blood flow of the individual in the derivative waveform;
an analysis circuitry configured to determine a stroke volume of the individual based on a function of the skew metric of the first derivative; and
a display configured to display physiological information based on the determined stroke volume.

2. The system of claim 1, wherein the skew metric is determined for each pulse wave or from a pulse-ensemble average that is based on a plurality of the pulse waves.

3. The system of claim 1, wherein the pulse oximeter further comprises an identification circuitry that identifies individual pulse waves from at least one of the derivative waveform or a PPG waveform that is formed by the at least one PPG signal, wherein the pulse waves are approximately defined from a first upstroke to a second, adjacent upstroke in the corresponding waveform, each of the first and second upstrokes corresponding to an increase in blood volume caused by a heartbeat.

4. The system of claim 1, wherein the skew metric is determined using at least one of Pearson's skewness, Fisher-Pearson standardized moment coefficient, quartile-based measurements, distance skewness, Cyhelsky's skewness coefficients, or a morphological metric of the derivative waveform.

5. The system of claim 1, wherein the pulse waves are pulse waves detected from a finger of the individual.

6. The system of claim 1, wherein the stroke volume is determined based on at least one of a constant or a coefficient, the at least one of the constant or the coefficient being determined by observed historical data and/or characteristics of the at least one PPG signal.

7. The system of claim 1, wherein the skew metric is a calculated value that is indicative of a distribution of values in a data set that includes the data points that define the pulse wave in the derivative waveform.

8. A method for determining stroke volume of an individual by a pulse oximeter, the method comprising:
acquiring, using the pulse oximeter, at least one photoplethysmogram (PPG) signal of the individual from a pulse oximetry sensor, the at least one PPG signal corresponding to pulse waves detected by the pulse oximetry sensor from blood flow of the individual;
calculating, using the pulse oximeter, a first derivative of the at least one PPG signal, the first derivative forming a derivative waveform;
determining, using the pulse oximeter, a skew metric of the first derivative, wherein the skew metric is indicative of a symmetry or asymmetry of at least one of the pulse waves in the derivative waveform;
determining, using the pulse oximeter, a stroke volume of the individual based on a function of the skew metric of the first derivative; and
displaying, using a display, physiological information based on the determined stroke volume.

9. The method of claim 8, wherein the determining the skew metric of the first derivative includes determining the skew metric for each pulse wave or for a pulse-ensemble average that is based on a plurality of the pulse waves.

10. The method of claim 9, wherein the pulse waves are defined from a first upstroke to a second, adjacent upstroke, each of the first and second upstrokes corresponding to an increase in blood volume caused by a heart beat.

11. The method of claim 8, wherein the pulse waves are pulse waves detected from a finger of the individual.

12. The method of claim 8, wherein the determining the skew metric of the first derivative includes determining at least one of Pearson's skewness, Fisher-Pearson standardized moment coefficient, quartile-based measurements, distance skewness, Cyhelsky's skewness coefficients, or a morphological metric of the derivative waveform.

13. The method of claim 8, wherein the stroke volume is determined based on at least one of a constant or a coefficient, the at least one of the constant or the coefficient being determined by observed historical data and/or characteristics of the at least one PPG signal.

14. A pulse oximetry system for determining stroke volume of an individual, the system comprising:
a pulse oximetry sensor configured to generate a photoplethysmogram (PPG) signal, wherein the pulse oximetry sensor detects light attenuated by the individual; and
a pulse oximeter coupled to the pulse oximetry sensor, the pulse oximeter comprising:
at least one processor or circuit configured to determine a skew metric of a first derivative of the PPG signal of the individual, and determine a stroke volume of the individual based on a function of the skew metric of the first derivative, wherein the skew metric is indicative of a symmetry or asymmetry of at least one pulse wave detected from blood flow of the individual in first derivative of the PPG signal; and
a display configured to display physiological information based on the determined stroke volume.

15. The system of claim 14, wherein the skew metric is determined using at least one of Pearson's skewness, Fisher-Pearson standardized moment coefficient, quartile-based measurements, distance skewness, Cyhelsky's skewness coefficients, or a morphological metric of the derivative waveform.

16. The system of claim 14, wherein the stroke volume is determined based on at least one of a constant or a coefficient, the at least one of the constant or the coefficient being determined by observed historical data and/or characteristics of the at least one PPG signal.

* * * * *